United States Patent
Strong et al.

(10) Patent No.: US 9,551,642 B2
(45) Date of Patent: Jan. 24, 2017

(54) CHARACTERIZING IONIC AND NONIONIC CONDENSATION FROM A MIXED VAPOR STREAM

(71) Applicant: Athlon Solutions, LLC, Houston, TX (US)

(72) Inventors: Russell Strong, Houston, TX (US); Richard W. Saulnier, Needville, TX (US)

(73) Assignee: Athlon Solutions LLC, Houston, TX (US)

(*) Notice: Subject to any disclaimer, the term of this patent is extended or adjusted under 35 U.S.C. 154(b) by 272 days.

(21) Appl. No.: 14/517,430

(22) Filed: Oct. 17, 2014

(65) Prior Publication Data

US 2016/0109351 A1    Apr. 21, 2016

(51) Int. Cl.
| | |
|---|---|
| *G01N 15/06* | (2006.01) |
| *G01N 33/18* | (2006.01) |
| *G01N 33/22* | (2006.01) |
| *G01N 33/28* | (2006.01) |
| *G01N 31/00* | (2006.01) |

(52) U.S. Cl.
CPC .............. *G01N 15/06* (2013.01); *G01N 31/00* (2013.01); *G01N 33/18* (2013.01); *G01N 33/22* (2013.01); *G01N 33/2835* (2013.01)

(58) Field of Classification Search
CPC ............ G01N 15/06; G01N 2015/0668; G01N 15/0687;G01N 33/22; G01N 33/26; G01N 33/28; G01N 33/2835; G01N 33/2847; G01N 31/00
USPC ................................. 73/61.41, 61.71, 61.72
See application file for complete search history.

(56) References Cited

U.S. PATENT DOCUMENTS

| | | | | |
|---|---|---|---|---|
| 5,450,728 A | * | 9/1995 | Vora ..................... | B01D 5/0039 62/613 |
| 5,714,664 A | * | 2/1998 | Fearnside .............. | C10G 75/02 208/184 |

\* cited by examiner

*Primary Examiner* — Benjamin Schmitt
(74) *Attorney, Agent, or Firm* — Jeffrey L. Streets

(57) ABSTRACT

A method includes forming a mixed vapor supply stream (MVSS) including measured amounts of water vapor, hydrocarbon vapor, and a carrier gas. For multiple target temperatures, the method includes (i) cooling the MVSS to form a first liquid stream and a mixed vapor outlet stream (MVOS), (ii) cooling the MVOS to condense vapor and form a second liquid stream, (iii) measuring an amount of a selected component in the second liquid stream, and (iv) calculating an amount of the selected component in the first liquid stream as the difference between the measured amounts of the selected component in the MVSS and the second liquid stream. The amount of the selected component as a function of the target temperature is analyzed to identify a lowest temperature at which the first liquid stream is expected to contain none of the selected component other than an amount soluble in the first liquid stream.

21 Claims, 6 Drawing Sheets

CHARACTERIZING IONIC AND NONIONIC CONDENSATION FROM A MIXED VAPOR STREAM

BACKGROUND

Field of the Invention

The present invention relates to laboratory apparatus and method for characterizing ionic and nonionic condensation from a complex vapor stream.

Background of the Related Art

Since the first crude oil refineries began operating over 150 years ago, corrosion has been experienced in the vessels used to separate the crude oil into saleable products. Early technology involved a series of separation vessels called pipe stills that would sequentially remove fractions based on boiling point, increasing from lowest to highest. Since a high production rate was more important than the life of the equipment at that point in time, corrosion did not initially receive much focus. However, after the invention of the automobile, refineries became larger and more integrated with upgraded processes. Accordingly, the refinery downtime that was necessary to replace corroded equipment became more costly and corrosion control became more important.

Early attempts to control corrosion focused on filming inhibitors and use of ammonia. The ammonia was added to raise the pH of the overhead water, which contains hydrochloric acid (HCl) as a by-product of crude oil distillation. The classic hydrolysis of salt found in crude oil is shown in Equations (1), (2), and (3), below. The third reaction contributes very little to the HCl in the overhead, because the hydrolysis temperature of NaCl is higher than typical crude heater to fractionator transfer temperatures.

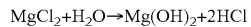  Equation (1):

$$MgCl_2 + H_2O \rightarrow Mg(OH)_2 + 2HCl$$

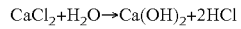  Equation (2):

$$CaCl_2 + H_2O \rightarrow Ca(OH)_2 + 2HCl$$

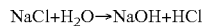  Equation (3):

$$NaCl + H_2O \rightarrow NaOH + HCl$$

Salting by ammonium chloride was recognized for its fouling and corrosion, but was initially dealt with by regular washing of equipment. However, washing required either a brief shutdown or a slowdown in operations, both of which became unacceptable as the economics of refinery operation became more competitive. Over time, other attempts at overhead corrosion control included the addition of alkaline metals or the addition of morpholine, which were intended to control the acidity of the first condensate. Originally this first condensate was characterized using equilibrium vapor pressures. It was recognized that as a pure compound, water would condense quickly from steam mixed with naphtha. The temperature at which water would begin to cascade out of the vapor became known as the Water Dew Point (WDP).

Despite the use of neutralizers and filming inhibitors, the corrosion problems in the overhead condensing equipment and in cold towers continued. A 1985 NACE survey showed that the average life for a bundle in overhead condensing service was about seven years. Various amines have also been used to control corrosion in the overhead condensing equipment, but have been found to cause the formation of amine chloride salts ahead of the WDP, similar to what was known to occur with ammonia in the presence of the HCl.

BRIEF SUMMARY

One embodiment of the present invention provides a method comprising forming a mixed vapor supply stream at a first elevated temperature, wherein the mixed vapor supply stream includes a measured amount of water vapor, a measured amount of hydrocarbon vapor, and a carrier gas. The method further comprises, for each of a plurality of target temperatures less than the first elevated temperature, (i) cooling the mixed vapor supply stream to a target temperature to form a first liquid stream and a mixed vapor outlet stream, (ii) cooling the mixed vapor outlet stream to condense vapor from the mixed vapor outlet stream to form a second liquid stream, (iii) measuring an amount of a selected component in the second liquid stream, and (iv) calculating an amount of the selected component in the first liquid stream as the difference between the measured amount of the selected component in the mixed vapor supply stream and the measured amount of the selected component in the second liquid stream. The method still further comprises analyzing the amount of the selected component as a function of the target temperature to identify a lowest temperature at which the first liquid stream is expected to contain none of the selected component other than an amount soluble in the first liquid stream.

DETAILED DESCRIPTION

Figure 1:
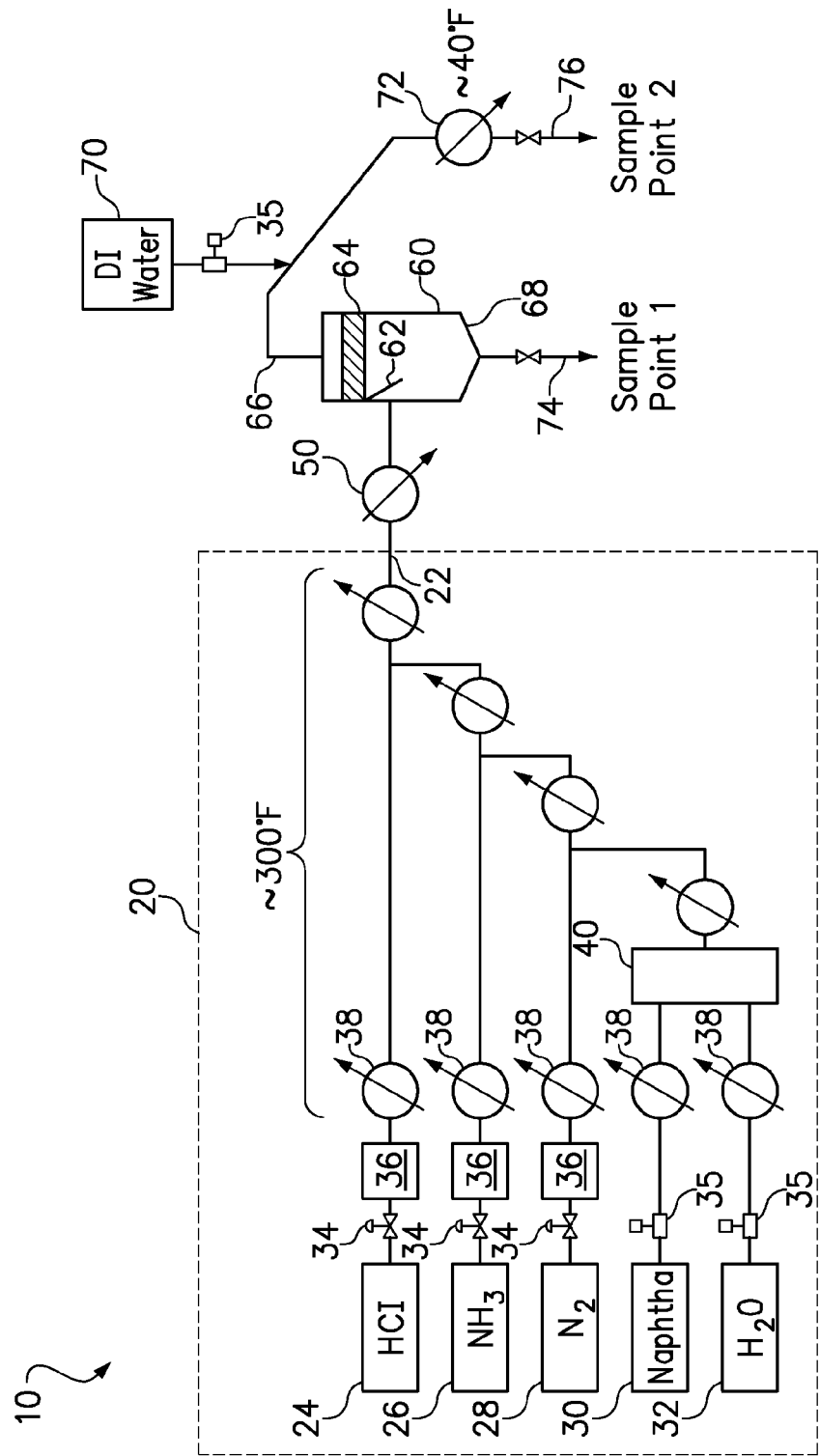
FIG. 1 is a diagram of an apparatus for determining a water dew point, ionic dew point and salt point of a complex mixture of vapors.

One embodiment of the present invention provides a method comprising forming a mixed vapor supply stream at a first elevated temperature, wherein the mixed vapor supply stream includes a measured amount of water vapor, a measured amount of hydrocarbon vapor, and a carrier gas. The method further comprises, for each of a plurality of target temperatures less than the first elevated temperature, (i) cooling the mixed vapor supply stream to a target temperature to form a first liquid stream and a mixed vapor outlet stream, (ii) cooling the mixed vapor outlet stream to condense vapor from the mixed vapor outlet stream to form a second liquid stream, (iii) measuring an amount of a selected component in the second liquid stream, and (iv) calculating an amount of the selected component in the first liquid stream as the difference between the measured amount of the selected component in the mixed vapor supply stream and the measured amount of the selected component in the second liquid stream. The method still further comprises analyzing the amount of the selected component as a function of the target temperature to identify a lowest temperature at which the first liquid stream is expected to contain none of the selected component other than an amount soluble in the first liquid stream.

The mixed vapor outlet stream is preferably cooled to condense substantially all of the condensable vapor in the mixed vapor outlet stream. In one option, the mixed vapor outlet stream may be cooled to a temperature that is less than the condensation temperature of the most volatile vapor in the mixed vapor outlet stream. Alternatively, the mixed vapor outlet stream may be cooled to room temperature, which may be a temperature in the range from 20 to 30 Celsius. Still further, the mixed vapor outlet stream may be cooled to a temperature below 20 Celsius since the objective is to condense and measure how much of each component is present in the second liquid stream. Additional cooling causes no problem in this regard. In fact, the mixed vapor outlet stream may be passed through an ice bath, which condenses vapor at a temperature near 0 Celsius.

In one option, the selected component is water. Accordingly, the method may further comprise defining the water dew point to be the lowest temperature at which the first liquid stream is expected to contain no free water or free aqueous phase. However, it should be recognized that the first liquid stream may contain some minor amount of water that is soluble in the hydrocarbon or organic phase at the system sample point pressure and temperature. The amount of water in the second liquid stream is measured at each of the plurality of target temperatures, and the dew point is the lowest temperature at which all of the water vapor of the mixed vapor supply stream ends up in the second liquid stream other than any amount of water that is in solution in the first liquid stream. At or above the water dew point temperature, the first liquid stream is substantially an organic phase with minor amounts of solubilized water. Furthermore, the mixed vapor supply stream does not include ionic components when measuring the water dew point, such that the condensation of water is not affected by the presence of ionic components.

In another option, the step of cooling the mixed vapor supply stream to a target temperature to form a first liquid stream and a mixed vapor outlet stream, includes maintaining the target temperature for a predetermined period of time to allow the second liquid stream to reach a steady state composition prior to measuring the amount of the selected component in the second liquid stream. The predetermined period of time needed to reach a steady state composition may depend upon the difference between the current target temperature and the previous target temperature. In other words, smaller temperature increments between target temperatures may require a smaller period of time to reach steady state than will larger temperature increments.

The mixed vapor supply stream is preferably cooled to each of the plurality of target temperatures by incrementally reducing the target temperature from the beginning of a test run to the ending of a test run. It is expected that the same results would be obtained by incrementally increasing the target temperature throughout the test run or by randomly changing the target temperature until each of the plurality of target temperatures was used.

Another embodiment of the present invention provides a method comprising forming a mixed vapor supply stream at a first elevated temperature, wherein the mixed vapor supply stream includes a measured amount of water vapor, a measured amount of hydrocarbon vapor, a measured amount of a hydrochloric acid vapor, a measured amount of vapor of a nitrogen-containing compound selected from ammonia and volatile amines, and a carrier gas. The method further comprises, for each of a plurality of target temperatures less than the first elevated temperature, (i) cooling the mixed vapor supply stream to a target temperature to form a first liquid stream and a mixed vapor outlet stream, (ii) cooling the mixed vapor outlet stream to condense vapor from the mixed vapor outlet stream to form a second liquid stream, (iii) measuring an amount of a selected component in the second liquid stream, and (iv) calculating an amount of the selected component in the first liquid stream as the difference between the measured amount of the selected component in the mixed vapor supply stream and the measured amount of the selected component in the second liquid stream. The method still further comprises analyzing the amount of the selected component as a function of the target temperature to identify a lowest temperature at which the first liquid stream is expected to contain none of the selected component other than an amount soluble in the first liquid stream.

The hydrocarbon may be any hydrocarbon stream of interest, such as in a study of corrosion mechanisms in a condenser. The hydrocarbon will typically a mixture of carbon-lengths, such as the mixture found in naphtha. The carrier gas is preferably an inert gas, such as nitrogen gas ($N_2$). The nitrogen-containing compound is selected from ammonia and volatile amines. The volatile amines may be selected from, without limitation, one or more of trimethylamine, cyclohexylamine, 3-methoxypropylamine, dimethylethanolamine, diethanolamine, dimethylisopropanolamine, dimethylamine, ethylenediamine, ethanolamine, morpholine, methylamine, methyldiethanolamine, dimethylethanolamine, dimethylaminopropanolamine, ethylamine, N-methylmorpholine, diglycolamine, diethylamine, buylamine, sec-butylamine, propylamine, dibutylamine, and N-ethylmorpholine.

Where the nitrogen-containing compound is a volatile amine, the mixed vapor supply stream may be formed differently than where the nitrogen-containing compound is ammonia. In the case of ammonia, the step of forming a mixed vapor supply stream at a first elevated temperature may include forming an intermediate mixed vapor supply stream including the water vapor, the hydrocarbon vapor, and the carrier gas, and then separately introducing the hydrochloric acid vapor and the ammonia into the intermediate mixed vapor supply stream so that the hydrochloric acid vapor and the ammonia are not allowed to mix together until after being introduced into the intermediate mixed vapor supply stream. If ammonia and the hydrochloric acid vapor are allowed to mix together outside of the intermediate mixed vapor supply stream, the ammonia and hydrochloric acid vapor may react and/or precipitate outside the test conditions and cause an invalid test result. Furthermore, the step of forming a mixed vapor supply stream at a first elevated temperature preferably includes separately heating the water vapor, the hydrocarbon vapor, the hydrochloric acid vapor, the vapor of the nitrogen-containing compound, and the carrier gas prior to combining the water vapor, the hydrocarbon vapor, the hydrochloric acid vapor, the vapor of the nitrogen-containing compound, and the carrier gas. Still further, the step of forming a mixed vapor supply stream at a first elevated temperature may include separately pressurizing the water vapor, the hydrocarbon vapor, the hydrochloric acid vapor, the vapor of the nitrogen-containing compound, and the carrier gas to a target pressure greater than atmospheric pressure before combining the water vapor, the hydrocarbon vapor, the hydrochloric acid vapor, the vapor of the nitrogen-containing compound, and the carrier gas.

Where the nitrogen-containing compound is a volatile amine, the step of forming a mixed vapor supply stream at a first elevated temperature may include mixing the volatile amine into liquid water, heating the mixture of the volatile amine and liquid water to form a mixture of amine vapor and water vapor, and combining the mixture of amine vapor and water vapor with the hydrocarbon vapor, the hydrochloric acid vapor and the carrier gas. Alternatively, the step of forming a mixed vapor supply stream at a first elevated temperature may include mixing the volatile amine into liquid hydrocarbon, heating the mixture of the volatile amine and liquid hydrocarbon to form a mixture of amine vapor and hydrocarbon vapor, and combining the mixture of amine vapor and hydrocarbon vapor with the water vapor, the hydrochloric acid vapor and the carrier gas.

In other embodiments, the selected component may be a plurality of selected components, such as where the selected components include water and chloride ion. It should be understood that while the mixed vapor supply stream may include a measured amount of hydrochloric acid vapor, an amount of hydrochloric acid that has condensed and is present in a liquid stream may be determined by measuring an amount of chloride ion. In particular, most corrosion problems in condensing units of hydrocarbon distillation units are attributed to, and can be associated with, the presence of chloride ions.

Depending upon the target temperature, the hydrochloric acid may remain in the vapor phase through a condenser and separator (i.e., knock out pot), end up being condensed into the second liquid stream, and quantified by measuring the chloride ions. As the target temperature is reduced from the elevated temperature of the mixed vapor supply stream, some of the hydrochloric acid may react with the ammonia or volatile amines to form salts that precipitate and exit the knock out pot in the first liquid stream. The initial occurrence of salt precipitation into the first liquid stream is evidenced by a reduced amount of chloride ion in the second liquid stream with no associated reduction in water in the second liquid stream. However, it is also possible that some salts will form in the vapor stream conduit between the knock out pot and a secondary condenser (e.g., an ice bath). Accordingly, a wash water is provided to wash any such salts from the conduit into the second liquid stream. In this manner, any difference between the chloride-content of the measured amount of hydrochloric acid in the mixed vapor supply stream and the chloride-content of the second liquid stream may be attributed to salt precipitation in the first liquid stream. This chloride mass balance allows the method to calculate the amount of salt in the first liquid stream as the difference between the measured amount of hydrochloric acid in the mixed vapor supply and the measured amount of chloride in the second liquid stream. One embodiment of the invention defines the "salt point" (SP) temperature to be the lowest temperature at which the first liquid stream is expected to contain less than a predetermined amount of the chloride measured in the mixed vapor supply stream. Optionally, the predetermined amount of the chloride may be expressed as a predetermined percentage of the chloride that was supplied in the mixed vapor supply stream. For example, the salt point may be the lowest temperature at which the first liquid stream is expected to contain less than 10% of the chloride in the mixed vapor supply stream. Alternatively, the predetermined percentage may be, without limitation, less than 8%, less than 5%, or less than 2%. The selection of a predetermined percentage may be influenced by the accuracy of the chloride measurements.

Optionally, the "salt point" temperature may be confirmed by a determination that the amount of water in the second liquid stream accounts for substantially all of the water vapor in the mixed vapor supply stream (i.e., there is no free water in the first liquid stream, just an amount of water that is soluble in the first liquid stream), and that the second liquid stream still contains more than zero but less than 50% of the measure of added chloride in the mixed vapor supply stream. Similarly, where a water wash is being used, the "salt point" temperature may be confirmed by a determination that the amount of water in the second liquid stream accounts for the water wash as well as all of the water vapor in the mixed vapor supply stream other than what was soluble in the first liquid stream. For this reason, the water wash is preferably run at a fixed and measured flow rate.

Where the selected components include water and chloride ion, the method may define the "ionic dew point" (iDP) to be the lowest temperature at which the first liquid stream is expected to contain an increasing amount of chloride and an increasing amount of water. An increasing amount of chloride and water in the first liquid stream is identified by measuring a decreasing amount of chloride and water in the second liquid stream. Alternatively, if the mixed vapor supply stream is known to include ionic components, such as hydrochloric acid and ammonia, then the method may define the ionic dew point to be the lowest temperature at which the first liquid stream is expected to contain no water.

The methods of the present invention may be used to identify the WDP, iDP and/or SP temperatures for a given composition of a mixed vapor supply stream. The method may be used, for example, to simulate the complex condensation profile of a crude unit overhead. Knowing the WDP, iDP and/or SP temperatures may, for example, help identify the locations within a refinery process where corrosion problems are expected to exist, or enable thermal management to control the location of corrosive conditions. The methods may also be used to provide measurements of WDP, iDP and/or SP temperature that will improve or validate the accuracy of computer models.

FIG. 1 is a diagram of an apparatus 10 for determining a water dew point, ionic dew point and salt point of a complex mixture of vapors. For example, the complex mixture may include components that will react with each other or form liquids that will absorb other components. The apparatus may be used, for example, to measure the temperature at which acidic salts, particularly from hydrochlorics, form in the vapor, and measure the material impact of those salts on the temperature at which water first forms as a condensate from the steam. The data obtained by the apparatus may be analyzed to determine the WDP, iDP and/or SP temperatures for a complex mixture of condensing fluids, acids and bases as may be found in a crude unit overhead.

The apparatus 10 includes a mixed vapor supply system 20 that forms a mixed vapor supply stream 22 at an elevated temperature and pressure. In the example shown, the apparatus includes a source of hydrochloric acid (HCl) 24, ammonia ($NH_3$) 26, nitrogen ($N_2$) 28, naphtha or synthesized naphtha 30 and water ($H_2O$) 32. The sources of hydrochloric acid (HCl) 24, ammonia ($NH_3$) 26, and nitrogen ($N_2$) 28 are each provided with a pressure regulator 34, a mass flow controller 36, and a heater 38 to produce individual gas or vapor streams at a selected elevated temperature and elevated pressure. The sources of naphtha or synthesized naphtha 30 and water ($H_2O$) 32 are each provided with a variable speed pump 35 and a heater 38 to produce vapor streams at a selected elevated temperature and elevated pressure. For example, the system 20 may supply each of these gas and vapor streams at an elevated temperature (~300 F) and an elevated pressure (~30 psig) before combining them. The naphtha vapor and water vapor are combined in a mixing vessel 40, then the naphtha/water vapor mixture is sequentially combined with nitrogen gas, ammonia vapor, and hydrochloric acid vapor with subsequent heating to at least maintain a temperature high enough to avoid condensation at any point in the system 20. The nitrogen gas serves as a non-condensable carrier gas.

As previously described, the method preferably brings each of the streams up to system temperature and pressure and then combines the gas and vapor streams in a sequence to control partial pressures of the gases and vapors so that, when combined, the temperature and pressure prevents the vapor streams from reacting to form salts or aqueous water. Volatile amines can be substituted for the ammonia gas by mixing the volatile amines into either the naphtha or the water.

The mixed vapor supply stream 22 from the mixed vapor supply system 20 is supplied to a cooler or condenser 50. The condenser 50 reduces the temperature of the mixed vapor supply stream from its elevated temperature (for example, 300 F) to a target temperature. The operation of the condenser 50 may be controlled to cool the mixed vapor supply stream to any of a plurality of target temperatures over a temperature range of interest. Preferably, the temperature range of interest will extend several degrees above and below a temperature determined by computer models or operational experience to be the WDP, iDP or SP, depending upon which one or more of these points is being determined. More specifically, the temperature range of interest may begin at the supply temperature of the mixed vapor supply stream and end at a reduced temperature after the sufficient data has been collected to enable one or more of these points to be determined through extrapolation or other type of data analysis.

Upon cooling the mixed vapor supply stream to a target temperature, the mixed vapor stream enters a separation vessel, such as a knock out pot 60. In this example, the knock out pot 60 includes an impingement plate 62 that directs the stream downward and a demister 64 made from stainless steel mesh. The impingement plate 62 and demister 64 are provided to prevent condensed liquid droplets and salt precipitates from exiting the knock out pot 60 in the mixed vapor outlet stream (overhead) 66. Accordingly, condensed liquid droplets and salt precipitates are allowed to settle to the bottom of the knock out pot 60, where a tapered surface 68 directs the liquid and/or salt to a Sample Point 1 (also referred to herein as the "first liquid stream") 74. Uncondensed vapors and gases exit the knock out pot 60 in the overhead conduit 66 (also referred to herein as the "mixed vapor outlet stream").

The knock out pot 60 may be thermally insulated or include heat tracing around inlet and outlet conduits to prevent temperature gradients away from the target temperature being controlled by the condenser 50. However, since it is possible that salts may precipitate within the overhead conduit 66, a source of deionized (DI) water may be supplied into the conduit at a controlled flow rate. As a result, any such salts are washed down the conduit along with the flow of uncondensed vapors and gases to a second condenser 72, which may take the form of an ice bath. Without the water wash flowing into overhead conduit 66 and into the second liquid stream 76, salts forming within the conduit at temperatures above the WDP might precipitate on the walls of the conduit and create a false positive for iDP.

The second condenser 72 should operate at a sufficiently cool temperature in order to condense all of the vapors remaining in the vapor stream. The liquids from the second condenser 72 are then collected at a Sample Point 2 (also referred to herein as the "second liquid stream") 76. There should be no vapor exiting the second condenser 72 and the only gas exiting the second condenser 72 is the noncondensable nitrogen gas.

Under steady state conditions, the entire mass of the mixed vapor supply stream provided to the knock out pot 60 must leave the knock out pot in either the first liquid stream 74 or the vapor stream 66. Since the second liquid stream 76 contains all of the condensed vapors of the vapor stream 66, the liquid samples collect at Sample Point 2 can be measured to indicate the composition of the vapor stream 66. The only differences in the composition of the vapor stream 66 and the composition of the second liquid stream 76 are those associated with the nitrogen gas and the deionized water used to wash the salt from the overhead conduit 66. Specifically, the nitrogen gas is in the vapor stream, but does not condense in the second liquid stream. Conversely, the deionized water used to wash the salt from the overhead conduit did not come from the mixed vapor supply stream and must be subtracted from the amount of water in the second liquid stream 76.

Subject to an adjustment for the amount of the water wash, any component of the mixed vapor supply stream (other than nitrogen gas) that does not end up in the second liquid stream must have precipitated as a salt at the target temperature in the condenser 50, the inlet conduit to the knock out pot, or the knock out pot, or to have condensed at the target temperature in the knock out pot. Accordingly, the amount of a selected component of the first liquid stream 74 can be determined by measuring the amount of the selected component in the second liquid stream 76 and then subtracting that measured amount of the selected component in the second liquid stream 76 from the measured amount of the selected component in the mixed vapor supply stream 22.

During a test run, a given composition of the mixed vapor supply stream 22 is formed and the condenser 50 is operated to cool the mixed vapor supply stream to each of a plurality of target temperatures. Preferably, the condenser 50 is controlled to incrementally reduce the target temperature of the mixed vapor supply stream entering the knock out pot 60, and to maintain each target temperature for a period of time to allow the system to reach steady state conditions in which the composition of the first and second liquid streams is representative of the temperature in the knock out pot 60 where the separation occurs. Samples of the first and second liquid streams are obtained and the amount of one or more selected components of the samples is measured. The data provides the amount of the one or more selected components as a function of temperature, which may be plotted and curve-fit to determine the onset of the WDP, the iDP or the SP as previously described.

In one specific example, the apparatus 10 is used as follows:

Turn on the heater(s) in the mixed vapor supply system 20 to ~300 F.

Turn on the condenser 50 to ~280 F.

Begin supplying nitrogen gas and naphtha vapor to the condenser, and hold until temperatures at multiple measuring points in the apparatus stabilize.

From initiation of the organic flow until completion of the test, samples are taken from the first and second liquid streams at 5 minute intervals.

Begin supplying water vapor into the mixed vapor supply stream and water wash into the overhead conduit.

Begin supplying hydrochloric acid vapor and either ammonia or volatile amine into the mixed vapor supply stream.

Once the system stabilizes (i.e., constant temperatures), the temperature of the condenser 50 is incrementally reduced, and samples are collected, until the temperature of the knock out pot 60 drops below a model-calculated water dew point (WDP), ionic dew point (iDP) or salt point (SP), whichever is the purpose of the run.

Once the measured amounts of selected components enable a determination of the WDP, iDP or SP temperature, then the test is completed.

Figure 2:
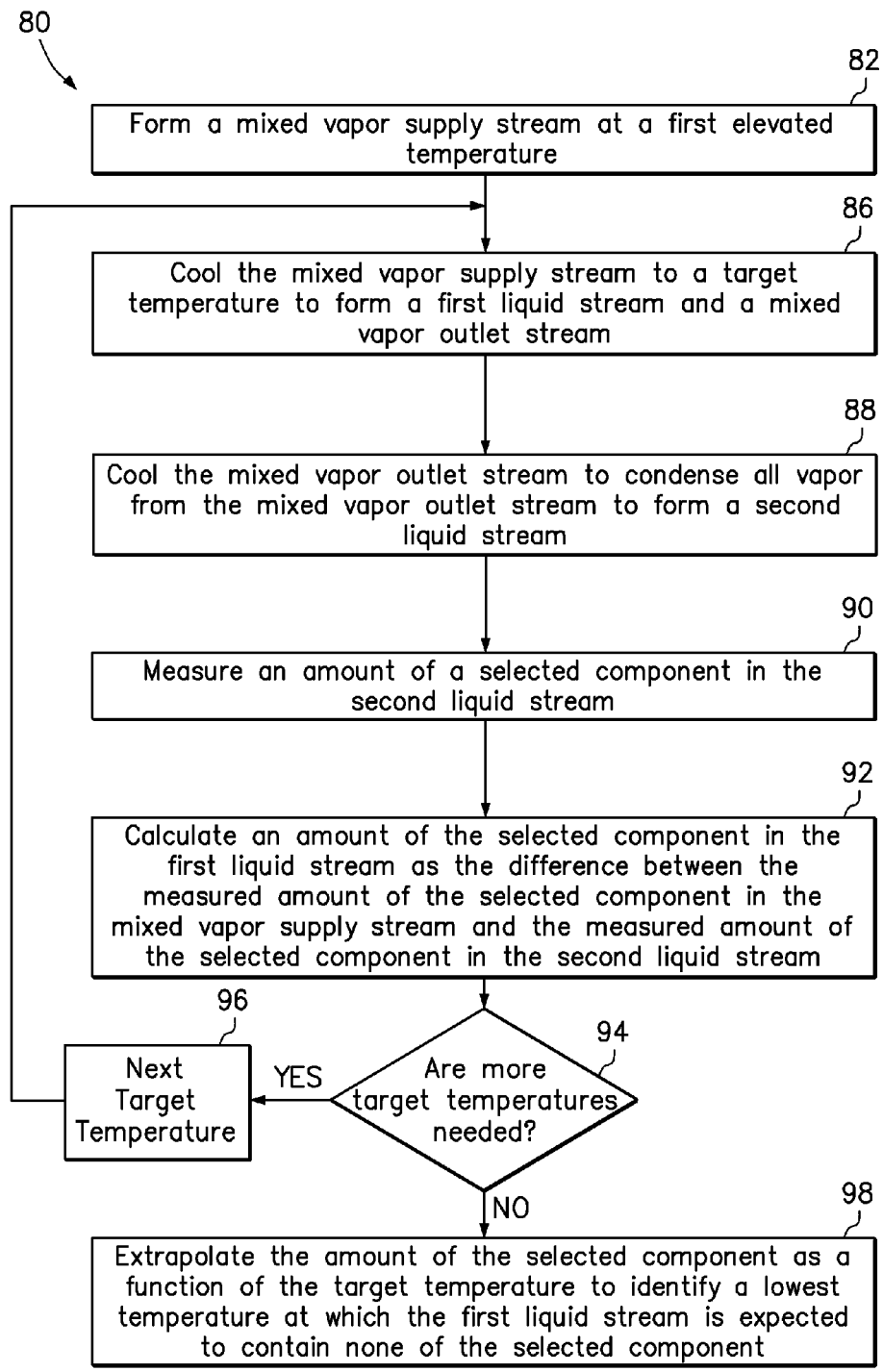
FIG. 2 is a flowchart of a method of determining a water dew point, an ionic dew point or a salt point temperature.

FIG. 2 is a flowchart of a method 80 of determining a water dew point, an ionic dew point or a salt point temperature. The method that can be used to demonstrate the onset of reactions and solubility relationships during a complex condensation and reaction environment, by focusing the analysis on measuring the absence of specific components separated in a vessel from the vapor by reaction or condensation. The sensitivity of the measurement is better measuring the material that remains in the mixed vapor outlet stream (overhead conduit) than trying to capture the exact temperature of reaction/condensation directly. The sensitivity of measurements on the mixed vapor outlet stream, as represented by the second liquid stream, is good enough to generate data that, by mathematical analysis (i.e., a second order polynomial curve fit and/or segmented data linear regressions but not limited to those forms) can be used to identify the onset temperature of the event.

The method 80 begins by forming a mixed vapor supply stream at a first elevated temperature in step 82. If the method is being used to identify a water dew point (nonionic) temperature, then the mixed vapor supply stream may include, for example, a measured amount of water vapor, a measured amount of hydrocarbon vapor, and a carrier gas. If the method is being used to identify a salt point temperature or an ionic dew point temperature, then the mixed vapor supply stream may further include a measured amount of hydrochloric acid vapor and either ammonia or a volatile amine.

In step 86, the mixed vapor supply stream is cooled to a target temperature to form a first liquid stream and a mixed vapor outlet stream. Step 88 cools the mixed vapor outlet stream to condense vapor from the mixed vapor outlet stream to form a second liquid stream. The nitrogen or other inert carrier gas is released after all of the vapor in the mixed vapor outlet stream has been condensed. An amount of a selected component in the second liquid stream is measured in step 90, which then allows step 92 to calculate an amount of the selected component in the first liquid stream as the difference between the measured amount of the selected component in the mixed vapor supply stream and the measured amount of the selected component in the second liquid stream. If step 94 determines that more target temperatures are needed to determine the temperature of interest (i.e., WDP, iDP or SP temperature), then step 96 causes the condenser to cool the mixed vapor supply stream to the next target temperature. If step 94 determines that no more target temperatures are needed, then the method moves to step 98 to extrapolate the amount of the selected component as a function of the target temperature to identify a lowest temperature at which the first liquid stream is expected to contain none of the selected component. For example, a mathematical determination of WDP and iDP may include a second order polynomial curve fit and/or segmented data linear regression.

Figure 3A:
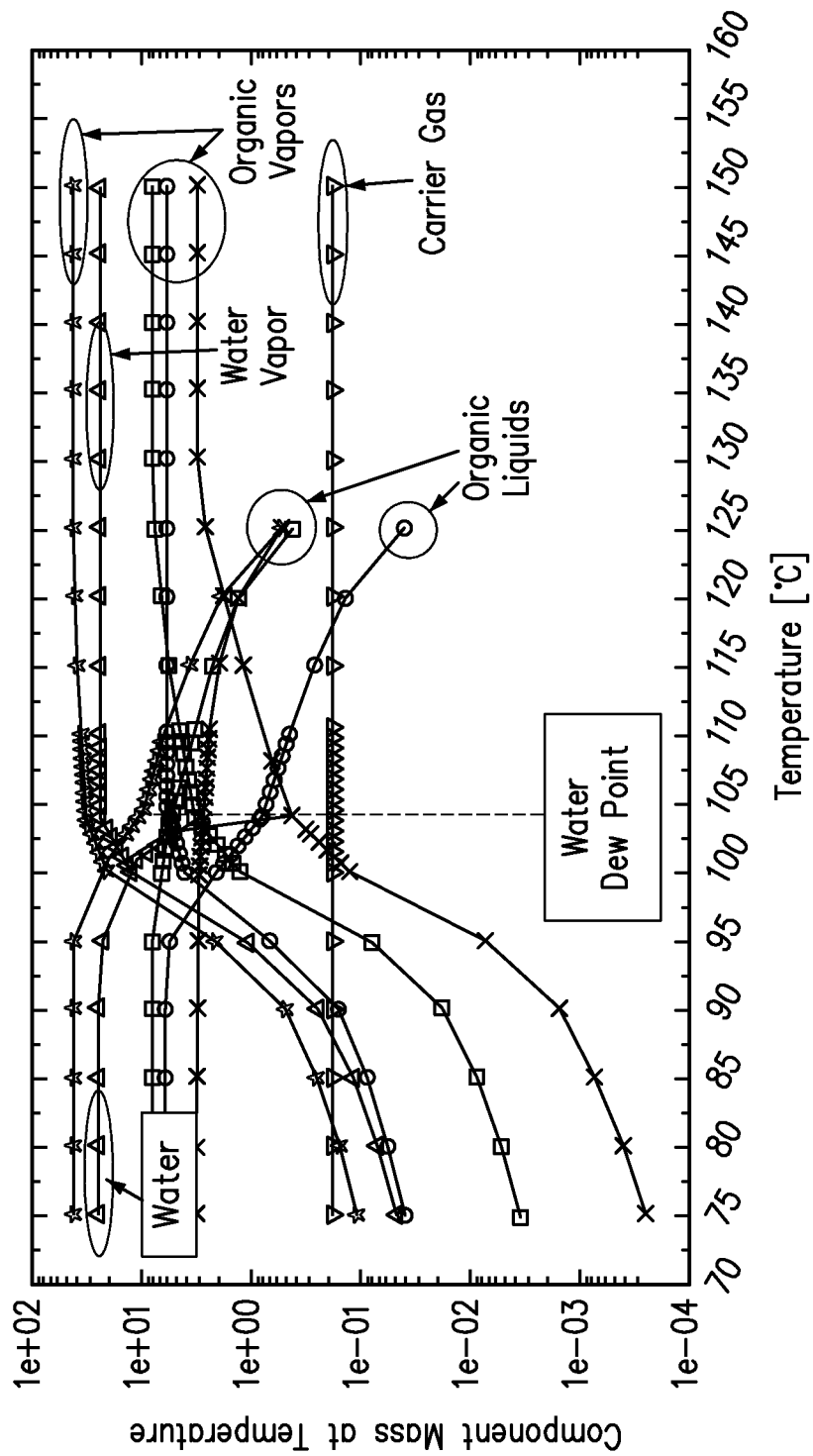
FIGS. 3A-3B are graphs of component concentration as a function of temperature for a nonionic mixture of vapors.
Figure 3B:
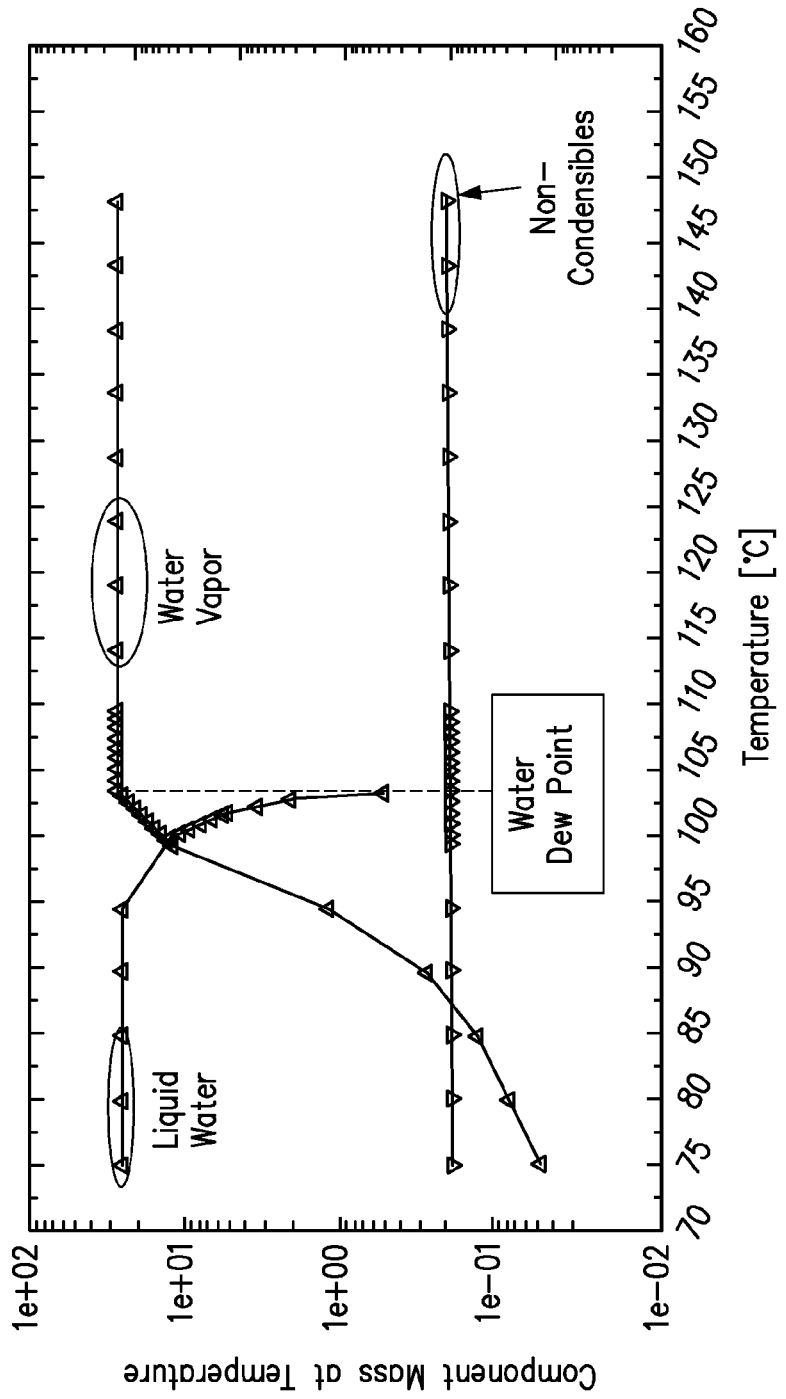

FIGS. 3A-3B are graphs of component amounts in the mixed vapor supply stream (labeled as "Organic Vapors", "Carrier Gas" and "Water Vapor") and the first liquid stream (labeled as "Organic Liquids" and "Water") as a function of temperature for a nonionic mixture of vapors in the mixed vapor supply stream. In the plurality of target temperatures, at any one target temperature the vapors present become the mixed vapor outlet stream and the liquids present become the first liquid. FIG. 3A shows all of the measured components of the mixed vapor outlet stream and the first liquid stream, including a number of separate organic components of the naphtha. It should be appreciated that the composition of the mixed vapor outlet stream in the overhead conduit out of the knock out pot changes significantly and dynamically, especially in the range between 95 and 105 degrees Celsius. The lowest temperature at which there is no free water in the first liquid stream is identified as the "Water Dew Point." In other words, the "Water Dew Point" is the temperature below which the first liquid stream will begin to contain free water.

FIG. 3B presents the same data as in FIG. 3A, except that the organic components of the mixed vapor supply stream have been excluded in order to emphasize the relationship between measured amounts of water in the vapor stream ("Water Vapor"), the calculation of an amount of water in the first liquid stream ("Liquid Water"), and mathematical analysis of the amounts of water in the second liquid stream to determine the water dew point (WDP) temperature. For a mixed vapor supply stream having a given amount of water, any reduction in the amount of water in the mixed vapor outlet stream, measured by seeing the reduction of water in the second liquid, indicates that water is condensing in the knockout pot. Referring to the graph in FIG. 3B, as the target temperature in the knock out pot is incrementally reduced, there is a point at about 100 degrees Celsius where the amount of water in the mixed vapor outlet stream begins to decline. In the plurality of target temperatures, this temperature would be defined as the water dew point (WDP) temperature. The vapors present at each of the plurality of target temperatures become the mixed vapor outlet stream and the liquids present become the first liquid. The condensable vapors in the mixed vapor outlet stream at each of the plurality of temperatures is condensed in the second condenser 72 and become the second liquid. Accordingly, at each of the plurality of temperatures below the WDP, the amount of water vapor in the mixed vapor outlet decreases, yielding less liquid water in the second liquid at each decreasing temperature, while the water in the first liquid increases by the same mass as is lost to the second liquid. The measured amount of water in the second liquid stream may then be mathematically analyzed by one of several methods to determine the temperature at which the first liquid stream is expected to have no free water, which is the same point at which the first liquid stream is expected to begin having free water. This temperature is referred to as the water dew point (WDP).

Various embodiments of the method include analyzing the data to identify the temperature at which one of the components, such as water, begins to drop out of the mixed vapor outlet stream (as measured in the second liquid stream) and end up in the first liquid stream. For example, the method may identify the temperature at which there is an inflection point in the measured amount of water in the second liquid stream, or the method may identify the temperature at which the calculated amount of water in the first liquid stream will begin to form a free water phase. It should be recognized that these two approaches are both directed at identifying the lowest temperature at which the first liquid stream is expected to contain none of the selected component other than an amount soluble in the first liquid stream. The data may be analyzed using various techniques including extrapolation (i.e., a second order polynomial curve fit and/or segmented data linear regressions but not limited to those forms).

Figure 4A:
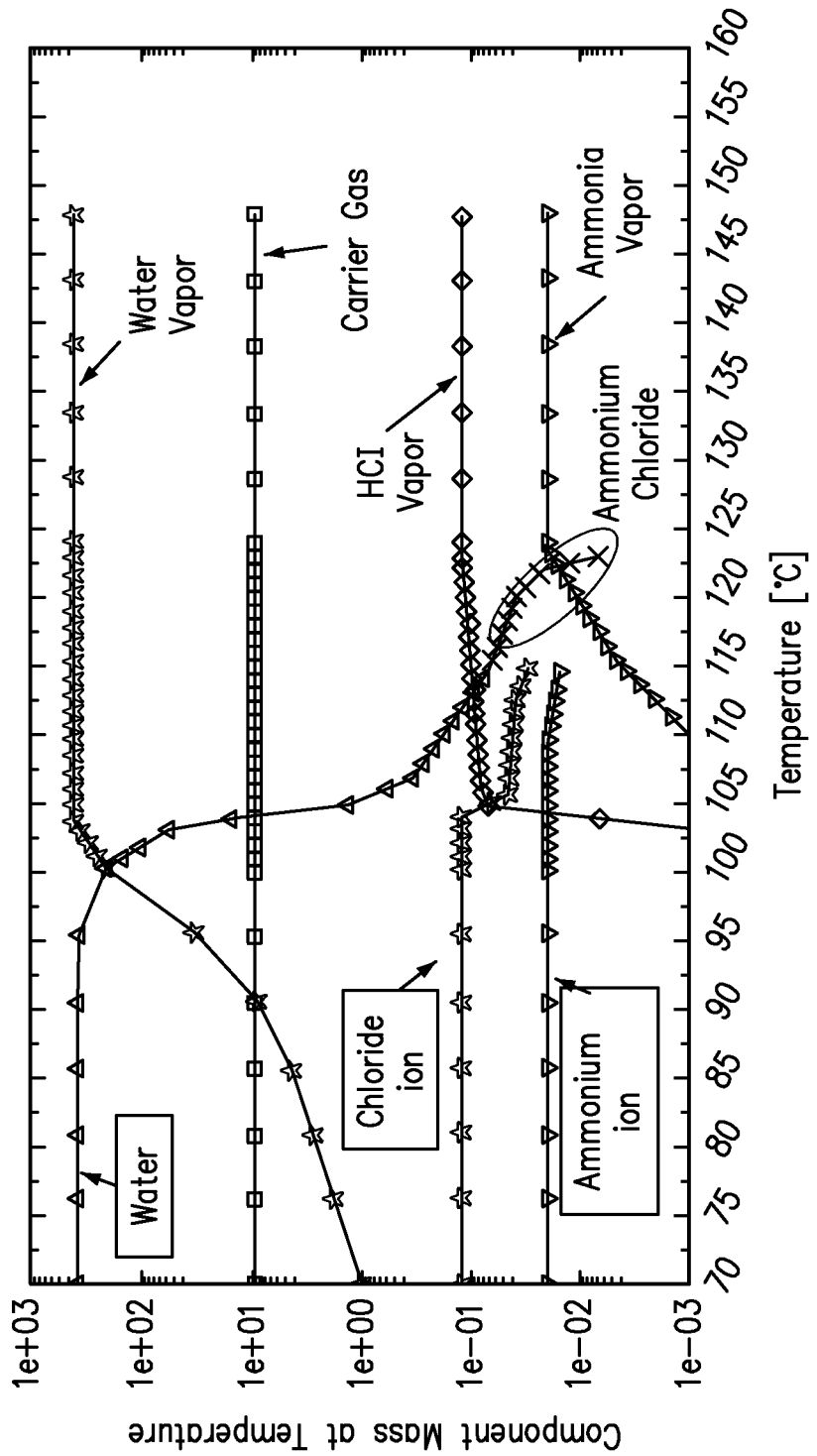
FIGS. 4A-4B are graphs of component concentration as a function of temperature for an ionic mixture of vapors.
Figure 4B:
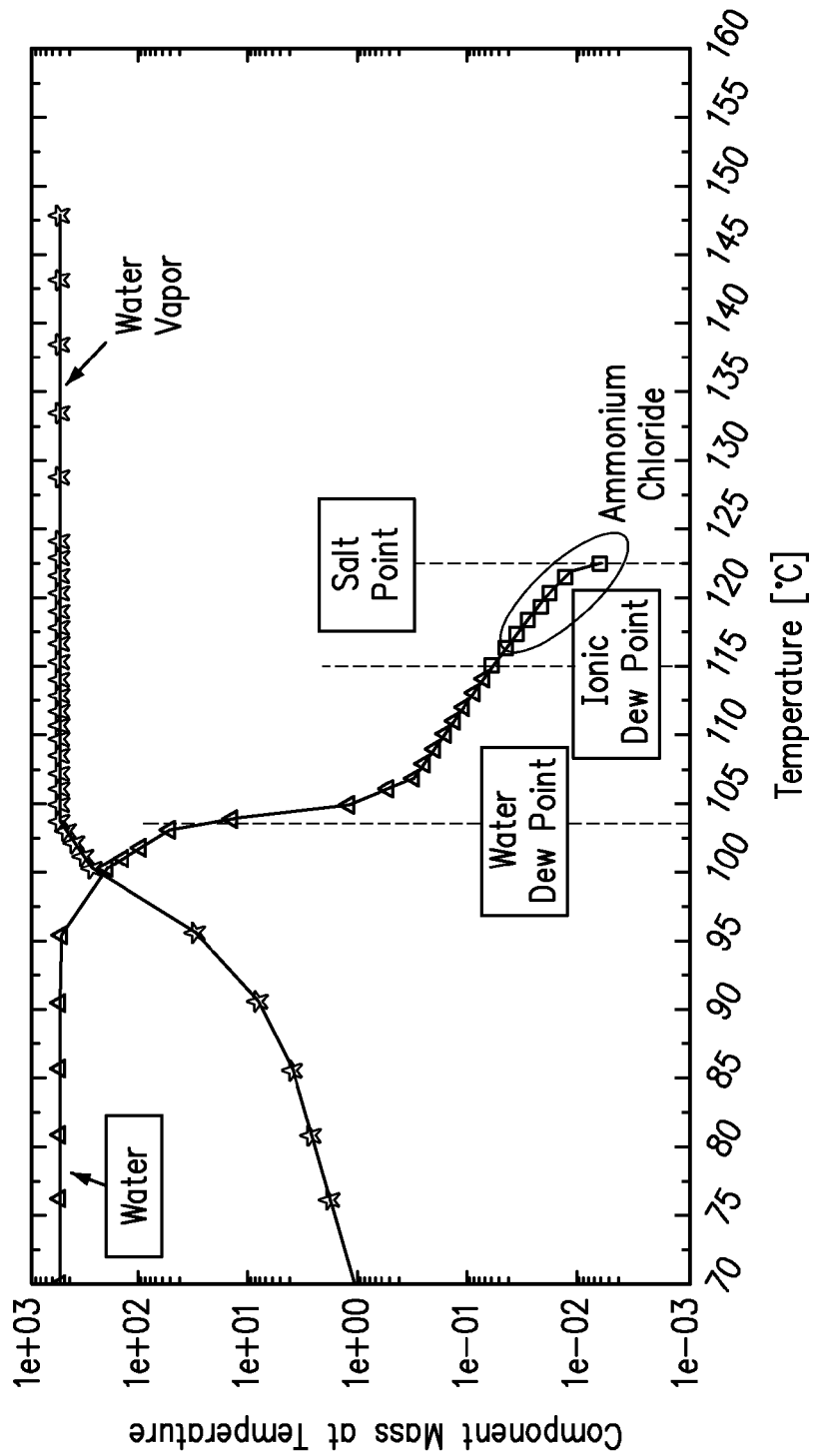

FIGS. 4A-4B are graphs of inorganic component amounts in the mixed vapor outlet stream, the first liquid stream as a function of temperature for an ionic mixture of vapors in the mixed vapor supply stream. For clarity, in order to emphasize the relationship between measured amounts of hydrochloric acid in the vapor stream and associated vapors, liquids and solids, FIG. 4A does not show the organic components. However, FIG. 4A does show the measured amounts of the non-organic components of the mixed vapor outlet stream and the calculated amounts of the inorganic components of the first liquid stream. It should be appreciated that the composition of the mixed vapor outlet stream in the overhead conduit out of the knock out pot changes significantly and dynamically. Due to the mixed vapor supply stream including hydrochloric acid vapor and ammonia, the mixed vapor outlet stream and first liquid stream also have changing amounts of ion and salt that affect the dew point of water.

FIG. 4B presents the same data as in FIG. 4A, but only including amounts of the water vapor in the mixed vapor outlet stream, liquid water calculated to be in the first liquid stream and the ammonium chloride salt in order to emphasize the relationship between water dew point (WDP), ionic dew point (iDP) and salt point (SP). As shown, the water dew point for the given mixed vapor supply stream is about 104 degrees Celsius, the ionic dew point for the given mixed vapor supply stream is about 115 degrees Celsius, and the salt point is about 124 degrees Celsius.

Referring to FIG. 3A, in this example organic liquids are present at a temperature above the salt point (SP) which is the norm. Referring to FIG. 4A, approximately 25% of the chloride has been removed from the mixed vapor outlet stream before the target temperature has dropped to the ionic dew point (iDP), and another 25% of the chloride has been removed before the target temperature has dropped to the water dew point (WDP). The amount of chloride that has been salted or lost to the first liquid stream may be calculated by subtracting the measured chloride value in the second liquid stream from the known amount of chloride added to the mixed vapor supply stream. The method of mathematical analysis to find the water dew point can also be applied to chloride measured in the second liquid water. The measured amount of chloride in the second liquid stream, at each of the plurality of temperatures, will remain constant until the target temperature has been lowered to the point of reaching the ionic dew point (iDP) or salt point (SP) and then will begin to reduce at lower temperatures. Using measured chloride values in the second liquid stream, a first or second order curve that intersects with the fixed chloride values will identify the ionic dew point (iDP) or salt point (SP) temperature.

As will be appreciated by one skilled in the art, various aspects of the methods disclosed above may be implemented or controlled by a computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, and/or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method, comprising:
   (a) forming a mixed vapor supply stream at a first elevated temperature, wherein the mixed vapor supply stream includes a measured amount of water vapor, a measured amount of hydrocarbon vapor, and a carrier gas; and
   (b) for each of a plurality of target temperatures less than the first elevated temperature:
      (i) cooling the mixed vapor supply stream to a target temperature to form a first liquid stream and a mixed vapor outlet stream;
      (ii) cooling the mixed vapor outlet stream to condense vapor from the mixed vapor outlet stream to form a second liquid stream;
      (iii) measuring an amount of a selected component in the second liquid stream; and
      (iv) calculating an amount of the selected component in the first liquid stream as the difference between the measured amount of the selected component in the mixed vapor supply stream and the measured amount of the selected component in the second liquid stream; and
   (c) analyzing the amount of the selected component as a function of the target temperature to identify a lowest temperature at which the first liquid stream is expected to contain none of the selected component other than an amount soluble in the first liquid stream.

2. The method of claim 1, wherein the selected component is water.

3. The method of claim 2, further comprising:
   defining the water dew point to be the lowest temperature at which the first liquid stream is expected to contain no separate phase of liquid water.

4. The method of claim 1, wherein cooling the mixed vapor supply stream to a target temperature to form a first liquid stream and a mixed vapor outlet stream, includes maintaining the target temperature for a predetermined period of time to allow the second liquid stream to reach a steady state composition prior to measuring the amount of the selected component in the second liquid stream.

5. The method of claim 1, wherein the mixed vapor supply stream is cooled to each of the plurality of target temperatures by incrementally reducing the target temperature.

6. The method of claim 1, wherein the mixed vapor supply stream further includes a measured amount of hydrochloric acid vapor and a measured amount of vapor of a nitrogen-containing compound selected from ammonia and volatile amines.

7. The method of claim 6, wherein the hydrocarbon is refined product naphtha or a synthesized naphtha from discrete hydrocarbon components.

8. The method of claim 6, wherein the carrier gas is an inert gas.

9. The method of claim 6, wherein the carrier gas is nitrogen gas.

10. The method of claim 6, wherein the nitrogen-containing compound is ammonia.

11. The method of claim 10, wherein the step of forming a mixed vapor supply stream at a first elevated temperature includes:
    forming an intermediate mixed vapor supply stream including the water vapor, the hydrocarbon vapor, and the carrier gas; and then
    separately introducing the hydrochloric acid vapor and the ammonia into the intermediate mixed vapor supply stream so that the hydrochloric acid vapor and the ammonia are not allowed to mix together until after being introduced into the intermediate mixed vapor supply stream.

12. The method of claim 11, wherein the step of forming a mixed vapor supply stream at a first elevated temperature includes:
separately heating the water vapor, the hydrocarbon vapor, the hydrochloric acid vapor, the vapor of the nitrogen-containing compound, and the carrier gas prior to combining the water vapor, the hydrocarbon vapor, the hydrochloric acid vapor, the vapor of the nitrogen-containing compound, and the carrier gas.

13. The method of claim 12, wherein the step of forming a mixed vapor supply stream at a first elevated temperature includes:
separately pressurizing the water vapor, the hydrocarbon vapor, the hydrochloric acid vapor, the vapor of the nitrogen-containing compound, and the carrier gas to a target pressure greater than atmospheric pressure before combining the water vapor, the hydrocarbon vapor, the hydrochloric acid vapor, the vapor of the nitrogen-containing compound, and the carrier gas.

14. The method of claim 6, wherein the nitrogen-containing compound is a volatile amine.

15. The method of claim 14, wherein the step of forming a mixed vapor supply stream at a first elevated temperature includes:
mixing the volatile amine into liquid water;
heating the mixture of the volatile amine and liquid water to form a mixture of amine vapor and water vapor;
combining the mixture of amine vapor and water vapor with the hydrocarbon vapor, the hydrochloric acid vapor and the carrier gas.

16. The method of claim 14, wherein the step of forming a mixed vapor supply stream at a first elevated temperature includes:
mixing the volatile amine into liquid hydrocarbon;
heating the mixture of the volatile amine and liquid hydrocarbon to form a mixture of amine vapor and hydrocarbon vapor;
combining the mixture of amine vapor and hydrocarbon vapor with the water vapor, the hydrochloric acid vapor and the carrier gas.

17. The method of claim 6, wherein the selected component is a plurality of selected components, and wherein the selected components includes water and chloride ion.

18. The method of claim 17, further comprising:
for each of the plurality of target temperatures, washing off walls of a conduit carrying the mixed vapor outlet stream to transfer any salt deposits into the second liquid stream prior to measuring the amount of chloride ion in the second liquid stream.

19. The method of claim 17, further comprising:
defining the ionic dew point to be the lowest temperature at which the first liquid stream is expected to contain an increasing amount of chloride and an increasing amount of water.

20. The method of claim 17, further comprising:
defining the ionic dew point to be the lowest temperature at which the first liquid stream is expected to contain no separate phase of liquid water.

21. The method of claim 17, further comprising:
defining the salt point to be the lowest temperature at which the first liquid stream is expected to first contain no chloride if the amount of water in the second liquid stream accounts for all of the water vapor in the mixed vapor supply stream.

* * * * *